United States Patent [19]

Bolin et al.

[11] Patent Number: 4,605,641
[45] Date of Patent: Aug. 12, 1986

[54] SYNTHETIC VASOACTIVE INTESTINAL PEPTIDE ANALOGS

[75] Inventors: David R. Bolin, Denville; Johannes A. Meienhofer, Upper Montclair; Iou-Iou Sytwu, Fanwood, all of N.J.

[73] Assignee: Hoffmann-La Roche Inc., Nutley, N.J.

[21] Appl. No.: 658,736

[22] Filed: Oct. 9, 1984

[51] Int. Cl.[4] .................. A61K 37/24; C07K 7/10
[52] U.S. Cl. ............................. 514/12; 530/324
[58] Field of Search ............... 260/112.5 R; 514/12

[56] References Cited

PUBLICATIONS

Chem. Pharm. Bull., vol. 28 (1980), 2265–2269.
Chem. Abstr., vol. 98 (1983), 17032h.
Chem. Abstr., vol. 95 (1981), 182578m.
Biochem. and Biophys. Res. Commun., vol. 121 (1984), 493–498.
Chem. Abstr., vol. 82 (1975), 38864r.
Chem. Abstr., vol. 100 (1984), 156971m.

Primary Examiner—Delbert R. Phillips
Attorney, Agent, or Firm—Jon S. Saxe; George M. Gould; Patricia A. Coburn

[57] ABSTRACT

Novel vasoactive intestinal peptide analogs containing substitutions of appropriately selected amino acids at specific positions of the VIP molecule, with potent sustained bronchodilatory activity without cardiovascular side effects.

29 Claims, No Drawings

SYNTHETIC VASOACTIVE INTESTINAL PEPTIDE ANALOGS

BACKGROUND OF THE INVENTION

Vasoactive intestinal peptide (VIP) was first discovered, isolated and purified from porcine intestines. U.S. Pat. No. 4,119,110. The peptide has twenty-eight (28) amino acids and has extensive homology to secretin and glucagon. Carlquist, M. et al., Horm. Metabol. Res., 14, 28–29 [1982]. The amino acid sequence of VIP is as follows:

```
1                   5                        10
His—Ser—Asp—Ala—Val—Phe—Thr—Asp—Asn—Tyr—Thr—
                                          —Arg—Leu—Arg
15                  20                       25
Lys—Gln—Met—Ala—Val—Lys—Lys—Tyr—Leu—Asn—Ser—
                                          —Ile—Leu—Asn—NH_2
```

VIP is known to exhibit a wide range of biological activities throughout the gastrointestinal tract and circulatory system. In light of its similarity to gastrointestinal hormones, VIP has been found to stimulate pancreatic and biliary secretion, hepatic glycogenolysis, glucagon and insulin secretion and to activate weakly pancreatic bicarbonate release. Kerrins, C. and Said, S. I., Proc. Soc. Exp. Biol. Med., 142, 1014–1017 (1972), Domschke, S., et al. Gastroenterology, 73, 478–480 (1977).

Neurons containing VIP have been localized by immunoassay in cells of the endocrine and exocrine systems, intestine and smooth muscle. Polak, J. M. et al. Gut, 15, 720–724 (1974). VIP has been found to be a neuroeffector causing the release of several hormones including prolactin (Frawley, L. S., et al., Neuroendocrinology 33; 79–83 (1981)), thyroxine (Ahren, B. et al., Nature, Lond. 287; 343–345 (1980)), and insulin and glucagon Schebalin, M. et al., Am. J. Physiol. E. 232; 197–200 (1977). VIP was also found to stimulate renin release from the kidney in vivo and in vitro. Porter, J. P. et al., Neuroendocrinology 36; 404–408 (1983). VIP has subsequently been found to be present in nerves and nerve terminals in the airways of various animal species and man. Dey, R. D. and Said, S. I. Fed. Proc. 39, 1962 (1980), Said, S. I., Kitamura, S., Yoshida, T., Preskitt, J., and Holden, L. D., Ann. N.Y. Acad. Sciences 221, 103–114, (1974). VIP's cardiovascular and bronchopulmonary effects are of interest as VIP has been found to be a powerful vasodilator and potent smooth muscle relaxant, acting on peripheral, pulmonary, and coronary vascular beds, Said, S. I., et al. Clin. Res. 20, 29 (1972). VIP has recently been found to have a vasodilatory effect on cerebral blood vessels. Lee, T. J. and Berczin, I., Science, 224, 898–900 (1984). In vitro studies demonstrated that exogenously applied vasoactive intestinal peptide to cerebral arteries induced vasodilation suggesting VIP as a possible transmitter for cerebral dilation. Lee, T. and Saito, A., Science 224, 898–901 (1984).

VIP has also been found to relax smooth muscle. Since it is normally present in airway tissues, as noted above, it is hypothesized that it may be an endogenous promotor of bronchial smooth muscle relaxation. Dey, R. D. and Said, S. I., Fed. Proc., 39, 1962 (1980). In vitro and in vivo testing have shown VIP to relax tracheal smooth muscle and protect against bronchoconstrictor agents such as histamine and prostaglandin $F_{2\alpha}$.

Wasserman, M. A. et al. in Vasoactive Intestinal Peptide, ed, S. I. Said, 177–184, Raven Press, N.Y. 1982, Said, S. I. et al. Ann. N.Y. Acad. Sci. 221, 103–114 (1974). VIP, when given intravenously, has been found to protect against bronchoconstrictor agents such as histamine, prostaglandin $F_{2\alpha}$, leukotriene, platelet activating factor as well as antigen-induced bronchoconstrictions. Said, S. I. et al., supra, 1982. However, when given by intravenous administration there are also cardiovascular effects including tachycardia and hypotension, not acceptable for use as a pharmaceutical. VIP, substituted at position 8 with glutamic acid in place of aspartic acid, was found to be less potent than VIP in effecting pancreatic secretion. Takeyama et al., Chem. Pharm. Bull., 28(7), 2265 (1980). No other amino acid substitutions in the VIP molecule have been disclosed in the prior art.

VIP when administered by aerosol to humans has been somewhat inconsistent in ameliorating histamine bronchoconstriction. Altieri et al., Pharmacologist, 25, 123 (1983). VIP given by inhalation to humans was found to have no significant effect on baseline airway function but did have a protective effect against histamine-induced bronchoconstriction. Barnes, P. J. and Dixon, C. M. S., Rev. Resp. Dis. 130; 162–166 (1984). VIP when given by aerosol displayed no tachycardia or hypotensive effects in conjunction with the bronchodilation. Said, S. I. et al., in *Vasoactive Intestinal Peptides*, edited by S. I. Said, pp. 185–191, Raven Press, N.Y., 1982. In addition, VIP has failed to relax bronchial smooth muscle in in vitro experiments, Davis et al. 1982.

SUMMARY OF THE INVENTION

The present invention relates to novel peptides of the formula:

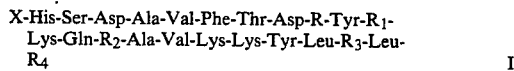

I wherein R represents Asn or Ala; $R_1$ represents Thr-Arg-Leu-Arg, Thr-Lys-Leu-Lys, Thr-Arg-Leu-Lys, Thr-Orn-Leu-Arg, Thr-Lys-Leu-Arg, or -Ser-Arg-Phe-Arg; $R_2$ represents Leu, Ile or Nle; $R_3$ represents Asn-Ser-Ile, Asn-Thr-Ile, Thr-Ser-Ile or Asn-Ser-Val; and, $R_4$ represents Asn-NH$_2$ or Thr-NH$_2$; and, X represents hydrogen or acetylation at the amino terminal and the pharmaceutically acceptable acid or base addition salts thereof.

More particularly the present invention relates to novel peptides of the formula:

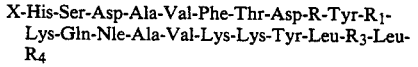

wherein X, R, $R_1$, $R_3$ and $R_4$ are as described above.

The peptides of the invention are useful in producing sustained relaxation of trachobronchial smooth muscle without cardiovascular side effects and thus are useful in the treatment of bronchoconstrictive disorders such as asthma.

DETAILED DESCRIPTION OF THE INVENTION

The present invention relates to novel analogs of vasoactive intestinal peptide (VIP), comprising substitutions of appropriately selected amino acids at certain specific positions of the VIP molecule. These analogs have enhanced sustainable bronchodilation activity without observable side effects. The peptides of this invention can be conveniently represented by formula I.

The nomenclature used to define the peptides is that typically used in the art wherein the amino group at the N-terminus appears to the left and the carboxyl group at the C-terminus to the right. By natural amino acid is meant one of the naturally occurring amino acids found in proteins comprising Gly, Ala, Val, Leu, Ile, Ser, Thr, Lys, Arg, Asp, Asn, Glu, Gln, Cys, Met, Phe, Tyr, Pro, Trp and His. By Nle is meant norleucine. By Orn is meant ornithine. Where the amino acid residue has isomeric forms, it is the L-form of the amino acid that is represented unless otherwise expressly indicated. The suffixes "—OH" and "—NH$_2$" following VIP refer to the free acid and amide forms of the polypeptide, respectively. In the event neither suffix is used, the expression is intended to encompass both forms. Analogs of VIP are indicated by setting forth the substituted amino acid in parentheses before "VIP"; that is, for example, "(Nle$^{17}$)-VIP" indicates a polypeptide having an amino acid sequence corresponding to VIP in which a norleucine residue has been substituted for methionine at position 17.

In a preferred embodiment of this invention the methionine residue at position 17 of the VIP molecule can be replaced by a different appropriately selected amino acid residue producing sustained bronchodilation. In particular, it was found that the VIP polypeptide in which the methionine residue at position 17 has been replaced by a norleucine residue has enhanced biological activity by relaxing bronchial smooth muscle. Replacement at this position was chosen to eliminate the oxidation side reactions which accompany methionine containing peptides. Norleucine was selected particularly because sterically it should present the least perturbation to the overall structure.

Substitutions at other positions of the VIP molecule have also been found to produce a peptide having the enhanced biological action of producing sustained bronchodilation. Positions 9, 11, 12, 13, 14, 26 and 28 may be selected for substitution by a different appropriately selected amino acid. Amino acids for substitution at those positions could be selected from the group including serine, phenylalanine, lysine, alanine, threonine, orthinine and valine. Furthermore, it was found that acetylation of the peptide at the amino terminal in conjunction with substitution at one of the selected positions with an appropriately selected amino acid has sustained bronchodilatory activity.

The invention provides for synthetic peptides having the following sequence:

X-His-Ser-Asp-Ala-Val-Phe-Thr-Asp-R-Tyr-R$_1$-Lys-Gln-R$_2$-Ala-Val-Lys-Lys-Tyr-Leu-R$_3$-Leu-R$_4$   I wherein R represents Asn or Ala; R$_1$ represents Thr-Arg-Leu-Arg, Thr-Lys-Leu-Lys, Thr-Arg-Leu-Lys, Thr-Orn-Leu-Arg, Thr-Lys-Leu-Arg, or -Ser-Arg-Phe-Arg; R$_2$ represents Leu, Ile, or Nle; R$_3$ represents Asn-Ser-Ile, Asn-Thr-Ile, Thr-Ser-Ile or Asn-Ser-Val; and, R$_4$ represents Asn-NH$_2$ or Thr-NH$_2$; and, X represents hydrogen or acetylation at the amino terminal and the pharmaceutically acceptable acid or base addition salts thereof.

More particularly, representative compounds of the present invention include peptides having the following amino acid sequences:

(Nle$^{17}$)-VIP
(Ala$^9$, Nle$^{17}$)-VIP
(Nle$^{17}$, Thr$^{25}$)-VIP (Nle$^{17}$, Thr$^{28}$)-VIP
(Nle$^{17}$, Thr$^{24}$)-VIP
(Lys$^{14}$, Nle$^{17}$)-VIP (Orn$^{12}$, Nle$^{17}$)-VIP
(Nle$^{17}$, Val$^{26}$, Thr$^{28}$)-VIP
(Lys$^{12}$, Nle$^{17}$)-VIP (Ser$^{11}$, Phe$^{13}$, Nle$^{17}$)-VIP
(Lys$^{12}$, Nle$^{17}$, Val$^{26}$, Thr$^{28}$)-VIP
(Lys$^{12}$, Lys$^{14}$, Nle$^{17}$, Val$^{26}$, Thr$^{28}$)-VIP
Ac-(Nle$^{17}$)-VIP

Ac-(Lys$^{12}$, Nle$^{17}$)-VIP
Ac-(Ser$^{11}$, Phe$^{13}$, Nle$^{17}$)-VIP

The above representative compounds may be readily synthesized by any known conventional procedure for the formation of a peptide linkage between amino acids. Such conventional procedure includes, for example, any solution phase procedure permitting a condensation reaction between the free alpha amino group of an amino acid or residue thereof having its carboxylic group or other reactive groups protected and the free primary carboxylic group of another amino acid or residue thereof having its amino group or other reactive groups protected.

The process for synthesizing the representative compounds may be carried out by a procedure whereby each amino acid in the desired sequence is added one at a time in succession to another amino acid or residue thereof or by a procedure whereby peptide fragments with the desired amino acid sequence are first synthesized conventionally and then condensed to provide the desired peptide.

Such conventional procedures for synthesizing the novel compounds of the present invention include for example any solid phase peptide synthesis method. In such a method the synthesis of the novel compounds can be carried out by sequentially incorporating the desired amino acid residues one at a time into the growing peptide chain according to the general principles of solid phase methods Merrifield, R. B., J. Am. Chem. Soc. 85, 2149–2154 (1963); Barany et al, The Peptides, Analysis, Synthesis and Biology, 2, Gross, E. and Meienhofer, J., Eds. Academic Press 1–284 (1980). In such embodiment, the peptides of this invention were assembled in a stepwise manner on a solid support using a Vega 250C peptide synthesizer. The chemistry module was controlled by a Zenith Z-89 microprocessor with manual operations at steps 2, 4, 16 and 20.

EXPERIMENTAL PROCEDURES AND METHODS REAGENTS

All solvents, methylene chloride (CH$_2$Cl$_2$), 2-propanol, and dimethylformamide, were Burdick & Jackson "Distilled in Glass" grade and used without additional distillation. Trifluoroacetic acid (TFA), diisopropylethylamine (DIPEA), and dicyclohexylcarbodiimide (DCC) were purchased from Chemical Dynamics Corp. and were "sequanal" grade purity. Hydroxybenzotriazole (HOBT) and 1,2-ethanedithiol (EDT) were purchased from Sigma Chemical Co. and used without further purification. All protected amino acids were of the L configuration and were obtained from Chemical Dynamics or Bachem.

Such syntheses typically protect the reactive side chain groups of the various amino acid moieties with suitable protecting groups which will prevent a chemical reaction from occurring at that site until the protecting group is ultimately removed. While specific protecting groups have been disclosed in regard to the solid phase synthesis aspect, it should be noted that each amino acid can be protected by any protective groups conventionally used for the respective amino acids in solution phase synthesis. Among such protecting groups there are included for example conventional protecting groups for carboxyl groups selected from esters such as aryl esters, particularly phenyl or phenyl substituted with lower alkyl, halo, nitro, thio or substituted thio, i.e., lower alkyl (1–7 carbon atoms) thio and the like. All α-amino groups were blocked with t-butyloxycarbonyl functions. Side chain groups were substituted as follows: Arg, His with p-toluene-sulfonyl; Asp, Ser, Thr with benzyl; Orn with benzyloxycarbonyl; Lys with 2-chlorobenzyloxycarbonyl; and Tyr with 2,6-dichlorobenzyl. Purity of these compounds was confirmed by thin layer chromotography (TLC) and optical rotation. The benzhydrylamine (BHA) resin was a copolymer of styrene—1% divinylbenzene in bead form (200–400 mesh) obtained from Beckman Instruments. Total nitrogen content was 0.654 meq/g.

The following instrumentation was utilized. Thin layer chromatography (TLC) was performed on glass backed precoated silica gel 60 F254 plates (Merck) using appropriate solvent systems. Detection of spots was by UV fluorescence quenching (254 nm absorption), iodine staining, or ninhydrin spray (for primary and secondary amines).

For amino acid analyses, peptides were hydrolyzed in 6N HCl containing 2–4 μl ethanedithiol at 115° C. for 24 hours in evacuated Reacti-Therm hydrolysis tubes. Analyses were performed on a Beckman 121M amino acid analyzer.

High performance liquid chromatography (HPLC) was conducted on an LDC apparatus consisting of a Constametric I pump, a Constametric III pump, a Gradient Master solvent programmer and mixer, and a Spectromonitor III variable wavelength UV detector. Analytical HPLC chromatography was performed on reversed phase with Waters Micro Bondapak $C_{18}$ columns (0.4×25 cm). Preparative HPLC separations were run on Whatman Magnum 20 partisil 10 ODS-3 columns (2×25 cm or 2×50 cm). In both cases, a precolumn of Whatman Co:Pell ODS pellicular packing was used.

Peptides were prepared using solid phase synthesis by the method generally described by Merrifield, J. Am. Chem. Soc., 85, 2149 (1963) although other equivalent chemical synthesis known in the art could also be used as previously mentioned. Solid-phase synthesis is commenced from the C-terminal end of the peptide by coupling a protected α-amino acid to a suitable resin. Such a starting material can be prepared by attaching an α-amino-protected amino acid by an ester linkage to a chloromethylated resin or a hydroxymethyl resin, or by an amide bond to a BHA resin or MBHA resin. Preparation of the hydroxymethyl resin is well known in the art. Chloromethylated resins are commercially available and their preparation is also well known in the art. BHA and MBHA resin supports are commercially available and generally used when the desired peptide being synthesized has an unsubstituted amide at the C-terminal.

The peptides were assembled in a stepwise manner on a solid support using a Vega 250C peptide synthesizer. The chemistry module was controlled by a Zenith Z-89 microprocessor with manual operations at steps 2, 4, 16 and 20.

Boc-Asn was coupled to the benzhydrylamine resin (3 g) using the preformed HOBt ester, formed from Boc-Asn (268 mg, 1.15 mmole), HOBt (213 mg, 1.57 mmole), and DCC (216 mg, 1.05 mmole) at 0° C. Loading was determined by amino acid analysis to be 0.27 mmole/g resin. Any unreacted amino groups were capped by treating with 6 equivalents each of acetic anhydride and pyridine.

The initial synthesis was started with 3 g of Boc-Asn-BHA resin and portions of peptide resin were removed at various points for separate analog preparation. The protocol for a typical synthetic cycle was as follows:

| Step | Reagent | Time |
|---|---|---|
| 1 | 1% EDT/$CH_2Cl_2$ | 1 × 30 sec |
| 2 | 50% TFA/$CH_2Cl_2$ w/1% EDT | 1 × 1 min |
| 3 | Repeat Step 1 | |
| 4 | 50% TFA/$CH_2Cl_2$ w/1% EDT | 1 × 15 min |
| 5 | $CH_2Cl_2$ | 1 × 30 sec |
| 6 | 2-Propanol | 1 × 30 sec |
| 7–8 | Repeat steps 5 & 6 | |
| 9 | $CH_2Cl_2$ | 2 × 30 sec |
| 10 | 8% DIPEA | 2 × 2 min |
| 11–15 | Repeat steps 5–9 | |
| 16 | 2 equiv. Boc—AA anhydride | 1 × 10 min |
| 17 | 1% DIPEA | 1 × 5 min |
| 18–19 | Repeat steps 6 & 9 | |
| 20–21 | Repeat steps 16 & 17 if Kaiser test is positive | |
| 22 | 2-Propanol | 1 × 30 sec |
| 23–24 | Repeat steps 5 & 6 | |
| 25 | $CH_2Cl_2$ | 1 × 30 sec |
| 26 | DMF | 2 × 30 sec |
| 27 | $CH_2Cl_2$ | 3 × 30 sec | wherein BOC represents t-butyloxycarbonyl, HOBt represents hydroxybenzotriazole, TFA represents trifluoroacetic acid, DIPEA represents diisopropylethylamine, DCC represents dicyclohexylcarbodiimide, EDT represents 1,2-ethanedithiol, DMF represents dimethylformamide and $CH_2Cl_2$ represents methylene chloride.

Solvents for all washings and couplings were measured to volumes of 10–20 ml/g resin. Most couplings were performed as the symmetrical anhydrides of the Boc-amino acids. They were preformed in $CH_2Cl_2$ at 0° C. in 15 min. using 4 equivalents of Boc-amino acid and 2 equivalents of DCC. Boc-Arg(Tos) was coupled as the symmetrical anhydride, however 25% dimethylacetamide (DMA)/$CH_2Cl_2$ was used as solvent. Boc-Asn and Boc-Gln were added as HOBt esters formed as stated above, in 25% DMA/$CH_2CL_2$. The removal of the Boc group from Boc-Gln-$^{16}$ peptide-BHA resin was modified by insertion of a 10% DIPEA/$CH_2Cl_2$ wash between steps 5 and 6 to minimize pyroglutamic acid formation.

Coupling reactions were monitored by the Kaiser ninhydrin test to determine whether coupling was complete after step 19. Kaiser, E. et al., Anal. Biochem., 34, 595–598 (1970). Slow reaction kinetics were noted for Boc-Arg-(Tos), Boc-Asn, and Boc-Gln and required up to 60 minutes in step 20 for completion. Total cycle times ranged from 85–135 minutes per residue.

The fully assembled peptide-resins were dried under high vacuum overnight. Deblocking and cleavage conditions were modified from Tam et al. *Tetrahedron Letters*, 23 2939–2942 (1982) and were optimized for VIP analogs generally. For each compound, the peptide-resin was treated in a Teflon HF apparatus (Peninsula) with 3 ml dimethylsulfide and approximately 1 ml HF at 0° C. for 2 hours. Volatile materials were removed by vacuum and 0.5 ml anisole was added. This mixture was treated with approximately 4.5 ml HF at 0° C. for 45 minutes and concentrated. The resin was washed with 2 volumes each of $EtO_2$ and EtOAc, then triturated with $4 \times 15$ ml 10% AcOH and filtered. Lyophilization of the aqueous filtrate yielded the crude peptide.

Preparative purifications were carried out directly on the crude peptide by HPLC on a Magnum 20 column. The peptides were applied in a minimum volume of 1% AcOH and eluted with a slow gradient (4 hr) of 0–40% 1% $AcOH/CH_3CN$ at a flow rate of 4.0 ml/min. Fractions were collected at 2.5 minute intervals and cuts made after inspection by analytical HPLC. Fractions judged to be greater than 99% pure were pooled and lyophilized. Yields of these single cuts less sideband material were 20–27% overall.

Purity of the individual peptides was checked by HPLC and determined to be 99% in all cases. Thin layer chromatography of each peptide showed single, homogeneous spots. Amino acid analyses of the individual peptides were performed and the expected values were obtained in each case.

The novel compounds of the present invention have valuable pharmacological properties. It will be shown that they are potent bronchodilators having no cardiovascular side effects. The bronchodilation produced by these novel peptides can be sustained for greater than two (2) hours. Thus being highly active bronchodilators, the compounds are valuable pharmaceutical agents for treatment of bronchoconstrictive disorders, e.g. asthma.

The novel compounds of formula I may be combined with various typical pharmaceutical carriers to provide compositions suitable for use in the treatment of bronchconstrictive disorders such as asthma. The dosage of these compounds is dependent upon various factors such as the particular compound employed and the particular formulation. An effective dosage can be determined by one of ordinary skill in the art from the effective concentrations ($EC_{50}$) disclosed herein.

Novel compounds of formula I form pharmaceutically acceptable acid addition salts with a variety of inorganic and organic acids such as sulfuric, phosphoric, hydrochloric, hydrobromic, hydroiodic, nitric, sulfamic, citric, lactic, pyruvic, oxalic, maleic, succinic, tartaric, cinnamic, acetic, trifluoroacetic, benzoic, salicyclic, gluconic, ascorbic and related acids.

The instant compounds may be administered by parenteral application either intravenously, subcutaneously, intramuscularly, orally or intranasally. A preferred form suitable for parenteral administration is by aerosol via oral or intranasal administration. The present invention is further illustrated by the examples which follow.

EXAMPLE 1

Preparation, Purification and Characterization of $(Nle^{17})VIP$

Boc-Asparagine (268 mg, 1.15 mmoles) and 1-hydroxybenzotriazole (213 mg, 1.57 mmoles) were dissolved in 10 ml dimethylacetamide and 10 ml methylyene chloride. This mixture was chilled to 0° C. and, with stirring, 216 mg (1.05 mmoles) dicyclohexylcarbodiimide was added. This solution was stirred for 30 minutes at 0° C. Separately, 3.0 g (1.53 mmoles) of benzhydrylamine copolystyrene—2% divinylbenzene cross-linked resin (0.51 mmole N/g) was washed with 8% diisopropylethylamine in methylene chloride for 30 minutes, filtered and washed with methylene chloride, dimethylformamide, and methylene chloride. The chilled solution above was added to the resin and stirred for 18 hours at room temperature. The resin was filtered and washed with methylene chloride, dimethylacetamide, isopropanol and methylene chloride. The resin was dried under high vacuum to give 3.0 g. Amino acid analysis showed the resin to contain 0.27 mmoles of asparagine/g. Unreacted amine groups were capped by shaking the resin with 2.0 ml acetic anhydride and 2.0 ml diisopropylethylamine in methylene chloride for 30 minutes. The resin was filtered and washed with methylene chloride, isopropanol, dimethylformamide and methylene chloride.

3.0 g (0.81 mmoles) of Boc-asparagine-resin was subjected to sequential solid phase synthesis using the above stated protocol. All couplings were performed using the symmetrical anhydrides or HOBt active esters of Boc-amino acids as described above. At steps 16 and 20 the activated Boc-amino acids were added with the corresponding reaction times as follows. Ten individual cycles were performed with Boc-leucine (807 mg, 3.24 mmole, 10 min; 807 mg, 324 mmole, 30 min), Boc-isoleucine (750 mg, 3.24 mmole, 10 mins; 750 mg, 3.24 mmole, 10 min), Boc-O-benzyl-serine (956 mg, 3.24 mmole, 10 min; 956 mg, 3.24 mmole, 10 min), Boc-asparagine (413 mg, 1.78 mmole, 10 min; 413 mg, 1.78 mmole, 60 min), Boc-leucine (807 mg, 3.24 mmole, 10 min; 807 mg, 3.24 mmole, 760 min), Boc-O-2,6-dichlorobenzyl-tyrosine (1.42 g, 3.24 mmole, 10 min, 1.42 g, 3.24 mmole, 60 min), Boc-$N^\epsilon$-2-chlorobenzyloxycarbonyl-lysine (1.34 g, 3.24 mole, 10 min; 1.34 g, 3.24 mmole, 20 min), Boc-$N^\epsilon$-2-chloro-benzyloxycarbonyl-lysine (1.34 g, 3.24 mmole, 10 min; 1.34 g, 3.24 mmole, 20 min), Boc-valine (703 mg, 3.24 mmole, 10 min; 703 mg, 324 mmole, 20 min), and Boc-alanine (612 mg, 3.24 mmole, 10 min; 612 mg, 3.24 mmole, 20 min) to give 4.8 g of Boc-undecapeptide resin.

4.1 g (0.694 mmole) of the resin was coupled with four individual cycles of Boc-norleucine (641 mg, 2.77 mmole, 10 min; 641 mg, 2.77 mmole, 20 min), Boc-glutamine (276 mg, 1.53 mmole, 10 min; 276 mg, 1.53 mmole, 60 min), Boc-$N^\epsilon$-2-chlorobenzyloxycarbonyl-lysine (1.15 g, 2.77 mmole, 10 min; 1.15 g, 2.77 mmole, 15 min) and Boc-$N^G$-tosyl-arginine (1.19 g, 2.77 mmole, 10 min; 1.19 g, 2.77 mmole, 10 min) to give 4.8 g of Boc-pentadecapeptide resin.

4.0 g (0.578 mmole) of this resin was coupled with one cycle of Boc-leucine (575 mg, 2.31 mole, 10 min; 575 mg, 2.31 mmole, 10 min) to give 4.1 g of Boc-hexadecapeptide resin.

3.23 g (0.462 mmole) of this resin was coupled with one cycle of Boc-$N^G$tosyl-arginine (795 mg, 1.85 mmole, 10 min; 795 mg, 1.85 mmole, 30 min) to give 3.2 g of Boc-heptadecapeptide resin.

1.6 g (0.231 mmole) of this resin was coupled with four individual cycles of Boc-O-benzyl-threonine (286 mg, 0.93 mmole, 20 min; 286 mg, 0.93 mmole, 10 min), Boc-O-2,6-dichlorobenzyl-tyrosine (407 mg, 0.93 mmole, 20 min; 407 mg, 0.93 mmole, 30 min), Boc-asparagine (119 mg, 0.51 mmole, 20 min; 119 mg, 0.51 mmole, 10 min), and Boc-$O^\beta$-benzyl-aspartic acid (299 mg, 0.93 mmole, 10 min; 299 mg, 0.93 mmole, 30 min) to give 1.9 g of Boc-uncosapeptide resin.

0.95 g (0.116 mmole) of this resin was coupled with six individual cycles of Boc-O-benzyl-threonine (144 mg, 0.46 mmole, 10 min; 144 mg, 0.46 mmole, 60 min), Boc-phenylalanine (123 mg, 0.46 mmole, 15 min; 123 mg, 0.46 mmole, 15 min), Boc-valine (101 mg, 0.46 mmole, 20 min; 101 mg, 0.46 mmole, 60 min), Boc-alanine (88 mg, 0.46 mmole, 15 min; 88 mg, 0.46 mmole, 10 min), Boc-$O^\beta$-benzyl-aspartic acid (150 mg, 0.46 mmole, 15 min; 150 mg, 0.46 mmole, 60 min), and Boc-O-benzyl-serine (187 mg, 0.46 mmole, 15 min; 187 mg, 0.46 mmole, 60 min) to give 0.98 g of Boc-heptacosapeptide resin.

350 mg (0.038 mmole) of this resin was coupled with one cycle of Boc-$N^{im}$-tosyl-histidine (63 mg, 0.15 mmole, 15 min; 63 mg, 0.15 mmole, 30 min) to give 383 mg of Boc-octacosapeptide resin.

353 mg (0.035 mmole) of this resin was cleaved by treatment with 5 ml liquid HF containing 0.25 ml 1,2-ethanedithiol and 0.25 ml anisole at 0° C. for 60 minutes. The HF was removed in vacuo and the residual solid was washed with ether, extracted with 10% acetic acid and lyophilized to give a white solid.

This crude material was purified by preparative HPLC on a Magnum-20 ODS-3 reversed-phase column as stated above. The main peak was collected and lyophilized to yield 30.7 mg (22%) or a white amorphous powder. This compound was homogeneous by HPLC and TLC and gave the correct amino acid analysis.

EXAMPLE 2

Preparation, Purification and Characterization of Ac-(Nle$^{17}$)VIP

A portion of the Boc-heptacosapeptide resin (230 mg, 0.032 mmole) of Example 1 was coupled with one cycle of Boc-$N^{im}$-tosyl-histidine (52 mg, 0.13 mmole, 10 min; 52 mg, 0.13 mmole, 10 min). The Boc-octacosapeptide resin was subjected to Steps 1 to 15 and then treated with 0.2 ml acetic anhydride and 0.2 ml diisopropylethylamine in methylene chloride for 30 minutes. Steps 22 to 27 were performed to give the acetyl-octacosapeptide resin.

145 mg (0.02 mmole) of this resin was cleaved with the modified Tam, supra., procedure. As described above, the resin was treated with 3 ml dimethylsulfide and 1 ml liquid HF for 2 hours at 0° C. The HF and dimethylsulfide were removed in vacuo. Anisole (0.5 ml) was added with 4.5 ml HF. The resin was stirred at 0° C. for 45 min and the HF was removed in vacuo. The residual oily solid was washed with ethyl acetate and ether and extracted with 10% acetic acid. The filtrate was lyophilized to yield 86 mg of an off-white solid.

This crude material was purified by preparative HPLC on a Magnum-20 ODS-3 reversed-phase column as stated above. The main peak was collected and lyophilized to yield 18.6 mg (26%) of a white, amorphous powder. This compound was homogeneous by HPLC and TLC and gave the correct amino acid analysis.

EXAMPLE 3

Preparation, Purification and Characterization of (Lys$^{12}$, Nle$^{17}$)-VIP

A portion of the Boc-hexadecapeptide resin (580 mg, 0.077 mole) of example 1 was coupled with twelve individual cycles of Boc-$N^\epsilon$-2-chlorobenzyloxycarbonyl-lysine (148 mg, 0.31 mmoles, 10 min; 148 mg, 0.31 mmoles, 10 min), Boc-O-benzyl-threonine (96 mg, 0.31 mmole, 10 min; 96 mg, 0.31 mmole, 10 min), Boc-O-2,6-Dichlorobenzyl Tyrosine (136 mg, 0.31 mmole, 10 min; 136 mg, 0.31 mmole, 10 min), Boc-asparagine (40 mg, 0.17 mmole, 30 min; 40 mg, 0.17 mmole, 30 min), Boc-$O^\beta$-benzyl-aspartic acid (100 mg, 0.31 mmole, 10 min; 100 mg, 0.31 mmole, 10 min), Boc-O-benzyl-threonine (96 mg, 0.31 mmole, 10 min; 96 mg, 0.31 mmole, 10 min), Boc-phenylalanine (82 mg, 0.31 mmole, 10 min; 82 mg, 0.31 mmole, 10 min), Boc-valine (67 mg, 0.31 mmole, 10 min; 67 mg, 0.31 mmole, 10 min), Boc-alanine (58 mg, 0.31 mmole, 10 min; 58 mg, 0.31 mmole, 10 min), Boc-$O^\beta$-benzyl-aspartic acid (100 mg, 0.31 mmole, 10 min; 100 mg, 0.31 mmole, 20 min), Boc-O-benzyl-serine (91 mg, 0.31 mmole, 10 min; 91 mg, 0.31 mmole, 20 min), and Boc-$N^{im}$-tosyl-histidine (127 mg, 0.31 mmole, 10 min; 127 mg, 0.31 mmole, 20 min) to give 573 mg of Boc-octacosapeptide resin.

290 mg (0.039 mmoles) of this resin was cleaved with the procedure described in Example 2. The HF was removed in vacuo and the residual oily solid was washed with ether and ethyl acetate. The residue was then extracted with 10% acetic acid and lyophilized to yield 149 mg of an off-white solid.

This crude material was purified by preparative HPLC on a Magnum-20 ODS-3 reversed-phase column as stated as above except that the aqueous solvent contained 0.2% triethylamine. The main peak was collected and lyophilized to yield 33 mg (24%) of a white, amorphous powder. This compound was homogeneous by HPLC and TLC and gave the correct amino acid analysis.

EXAMPLE 4

Preparation, Purification and Characterization of Ac-(Lys$^{12}$, Nle$^{17}$)VIP A portion of the Boc-octacosapeptide resin (290 mg, 0.039 mmoles) of Example 3 was subjected to steps 1 to 15 and then treated with 0.3 ml acetic anhydride and 0.3 ml diisopropyethylamine in methylene chloride for 30 minutes. Steps 22 to 27 were performed to give the acetyl-octacosapeptide resin.

This peptide resin was cleaved with the procedure described in Example 2. The HF was removed in vacuo and the residual gel was washed with ether and ethyl acetate. The residue was then extracted with 10% acetic acid and lyophilized to yield 123.4 mg of a white, hygroscopic solid.

This crude material was purified by preparative HPLC as in Example 2. The main peak was collected and lyophilized to yield 15.3 mg (11%) of a white, amorphous powder. This compound was homogeneous by HPLC and TLC and gave the correct amino acid analysis.

EXAMPLE 5

Preparation, Purification and Characterization of (Orn$^{12}$, Nle$^{17}$)VIP

A portion of the Boc-hexadecapeptide resin (290 mg, 0.038 mmole) of Example 1 was coupled with twelve individual cycles of Boc-N$^\delta$-benzyloxycarbonyl-ornithine (57 mg, 0.155 mmole, 15 min; 57 mg, 0.155 mmole, 30 min.), Boc-O-benzylthreonine (98 mg, 0.155 mmole, 15 min; 98 mg, 0.155 mmole, 30 min.), Boc-O-2,6-dichlorobenzyl-tyrosine (68 mg, 0.155 mmole, 15 min; 68 mg, 0.155 mmole, 30 min.), Boc-asparagine (20 mg, 0.08 mmole, 15 min., 20 mg, 0.08 mmole, 60 min.; 39 mg, 0.17 mmole, 60 min.), Boc-O$^\beta$-benzyl-aspartic acid (50 mg, 0.155 mmole, 15 min.; 50 mg, 0.155 mmole, 20 min.), Boc-O-benzylthreonine (98 mg, 0.155 mmole, 15 min.; 98 mg, 0.155 mmole, 90 min.), Boc-phenylalanine (41 mg, 0.155 mmole, 15 min.; 41 mg, 0.155 mmole, 10 min.), Boc-valine (34 mg, 0.155 mmole, 12 min.; 34 mg, 0.155 mmole, 60 min.), Boc-alanine (30 mg, 0.155 mmole, 15 min.; 30 mg, 0.155 mmole, 20 min.), Boc-O$^\beta$-benzyl-aspartic acid (50 mg, 0.155 mmole, 15 min; 50 mg, 0.155 mmole, 20 min.), Boc-O-benzylserine (46 mg, 0.155 mmole, 10 min.; 46 mg, 0.155 mmole, 60 min.), and Boc-N$^{im}$-tosyl-histidine (91 mg, 0.155 mmoles, 15 min., 91 mg, 0.155 mg, 0.155 mmoles, 30 min.) to give 305 mg of Boc-octacosapeptide resin.

This peptide resin was cleaved with the procedure described in Example 2. The HF was removed in vacuo and the residual gel was washed with ether and ethyl acetate. The residue was then extracted with 10% acetic acid and lyophilized to yield 150 mg of a white solid.

This crude material was purified by preparative HPLC as in Example 2. The main peak was collected and lyophilized to yield 19 mg (14%) of a white, amorphous powder. This compound was homogeneous by HPLC and TLC and gave the correct amino acid analysis.

EXAMPLE 6

Preparation, Purification and Characterization of (Ser$^{11}$, Phe$^{13}$, Nle$^{17}$)VIP A portion of the Boc-pentadecapeptide resin (800 mg, 0.116 mmole) of Example 1 was coupled with thirteen individual cycles of Boc-phenylalanine (123 mg, 0.46 mmole, 10 min.; 123 mg, 0.46 mmole, 10 min), Boc-N$^\epsilon$-tosylaryinine (200 mg, 0.46 mmole, 10 min; 200 mg, 0.46 mmole, 15 min.), Boc-O-benzyl-serine (137 mg, 0.46 mmole, 10 min.; 137 mg, 0.46 mmole, 10 min.), Boc-O-2,6-dichlorobenzyl-tyrosine (205 mg, 0.46 mmole, 10 min.; 205 mg, 0.46 mmole, 10 min.), Boc-asparagine (59 mg, 0.25 mmole, 30 min.; 59 mg, 0.25 mmole, 10 min.), Boc-O$^\beta$-benzyl-aspartic acid (150 mg, 0.46 mmole, 10 min., 150 mg, 0.46 mmole, 25 min.), Boc-O-benzyl-threonine (144 mg, 0.46 mmole, 15 min.; 144 mg, 0.46 mmole, 15 min.), Boc-phenylalanine (123 mg, 0.46 mmole, 10 min.; 123 mg, 0.46 mmole, 15 min.), Boc-valine (101 mg, 0.46 mmole, 10 min.; 101 mg, 0.46 mmole, 15 min.), Boc-alanine (88 mg, 0.46 mmoles, 10 min.; 88 mg, 0.46 mmole, 15 min.), Boc-O$^\beta$-benzyl-aspartic acid (150 mg, 0.46 mmole, 10 min.; 150 mg, 0.46 mmole, 15 min.), Boc-O-benzyl-serine (137 mg, 0.46 mmole, 10 min.; 137 mg, 0.46 mmole, 15 min.), and Boc-N$^{im}$-tosylhistidine (190 mg, 0.46 mmole, 10 min.; 190 mg, 0.46 mmole, 15 min.) to give 810 mg of Boc-octacosapeptide resin.

540 mg (0.077 mmole) of this resin was treated with 209 mg (1.55 mmole) 1-hydroxybenzotriazole in 25 ml dimethylacetamide for 1 hour. This resin was then carried through steps 1 to 15 and dried in vacuo to give 523 mg of peptide resin.

This peptide resin was cleaved by treatment with 0.25 ml anisole, 0.25 ml ethanedithiol, and 4.5 ml HF at 0° C. for 1 hr. The HF was removed in vacuo and the residue was washed with ether. The resin was extracted with 10% acetic acid and lyophilized to yield 170 mg of white solid.

The crude material was purified by preparative HPLC as in Example 2. The main peak was collected and lyophilized to yield 48.2 mg (17.2%) of a white, amorphous powder. This compound was found to be homogeneous by HPLC and TLC and gave the correct amino acid analysis.

EXAMPLE 7

Preparation, Purification and Characterization of Ac-(Ser$^{11}$, Phe$^{13}$, Nle$^{17}$)VIP A portion of the Boc-octacosapeptide resin (270 mg, 0.039 mmole) of Example 6 was subjected to steps 1 to 15 and then treated with 0.3 ml acetic anhydride and 0.3 ml of diisopropylethylamine in methylene chloride for 30 minutes. Steps 22 to 27 were performed to give the acetyl-octacosapeptide resin.

105 mg (0.026 mmole) of this peptide resin was cleaved with the procedure described in Example 2. The HF was removed in vacuo and the residual oil was washed with ether and ethyl acetate. This residue was then extracted with 10% acetic acid and lyophilized to yield 90 mg of a white solid.

This crude material was purified by preparative HPLC as in Example 2. The main peak was collected and lyophilized to yield 21.3 mg (22.7%) of a white, amorphous powder. This compound was homogeneous by HPLC and TLC and gave the correct amino acid analysis.

EXAMPLE 8

Preparation, Purification and Charaterization of (Nle$^{17}$, Thr$^{25}$)VIP

Benzhydrylamine copolystyrene-2% divinylbenzene cross-linked resin (10.0 g, 6.54 mmole N) was derivatized as in Example 1 with Boc-asparagine (885 mg, 3.81 mmole), 1-hydroxybenzotriazole (703 mg, 5.20 mmole), and dicyclohexylcarbodiimide (713 mg, 3.45 mmole). After washing, the resin was dried under high vacuum to give 9.425 g. Amino acid analysis showed the resin to contain 0.27 mmoles of asparagine/g. Unreacted amine groups were capped with 6.0 ml acetic anhydride and 6.0 ml diisopropylethylamine in methylene chloride for 30 minutes and washed as in Example 1.

A portion of this Boc-asparagine resin (0.44 g, 0.11 mmole) was coupled with twenty-seven individual cycles of Boc-leucine (109 mg, 0.44 mmoles, 15 min.; 109 mg, 0.44 mmole, 30 min.), Boc-isoleucine (101 mg, 0.44 mmole, 15 min.; 101 mg, 0.44 mmole, 10 min.), Boc-O-benzyl-threonine (136 mg, 0.44 mmole, 15 min.; 136 mg, 0.44 mmole, 10 min.), Boc-asparagine (56 mg, 0.29 mmole, 30 min., 56 mg, 0.24 mmole, 10 min.), Boc-leucine (109 mg, 0.44 mmole, 15 min., 109 mg, 0.44 mmole, 10 min), Boc-O-2,6-dichlorobenzyl-tyrosine (194 mg, 0.44 mmole, 30 min., 194 mg, 0.44 mmole, 60 min.; 388 mg, 0.88 mmole, 120 min.), Boc-N$^\epsilon$-2-chlorobenzyloxycarbonyl-lysine (183 mg, 0.44 mmole, 45 min.; 182 mg, 0.44 mmole, 10 min.), Boc-N$^\epsilon$-2-chlorobenzyloxycarbonyl-lysine (182 mg, 0.44 mmole, 45 min.; 182 mg, 0.44 mmole, 10 min.;), Boc-valine (95 mg, 0.44 mmole, 25 min.; 95 mg, 0.44 mmole, 10 min.), Boc-alanine (83 mg, 0.44 mmole, 15 min.; 83 mg, 0.44 mmole, 10 min.), Boc-norleucine (101 mg, 0.44 mmole, 15 min.; 101 mg, 0.44 mmole, 10 min.), Boc-glutamine (59 mg, 0.24 mmole, 30 min.; 59 mg, 0.24 mmole, 10 min.), Boc-N-2-chlorobenzyloxycarbonyl-lysine (182 mg, 0.44 mmole, 15 min.; 182 mg, 0.44 mmole, 15 min.), Boc-N-tosyl-arginine (188 mg, 0.44 mmole, 15 min.; 188 mg, 0.44 mmole, 60 min), Boc-leucine (109 mg, 0.44 mmole, 15 min.; 109 mg, 0.44 mmole, 30 min.), Boc-N-tosyl-arginine (377 mg, 0.88 mmole, 30 min.), Boc-O-benzyl-threonine (136 mg, 0.44 mmole, 15 min.; 136 mg, 0.44 mmole, 30 min.), Boc-O-2,6-dichlorobenzyl-tyrosine (194 mg, 0.44 mmole, 15 min; 194 mg, 0.44 mmole, 30 min.) Boc-asparagine (56 mg, 0.24 mmole, 30 min.; 56 mg, 0.24 mmole, 10 min.), Boc-O$^\beta$-benzyl-aspartic acid (142 mg, 0.44 mmole, 15 min.; 142 mg, 0.99 mmole, 10 min.), Boc-O-benzyl-threonine (136 mg, 0.44 mmole, 15 min.; 136 mg, 0.44 mmole, 10 min.), Boc-phenylalanine (233 mg, 0.88 mmole, 30 min.), Boc-valine (95 mg, 0.44 mmole, 15 min.; 95 mg, 0.44 mmole, 30 min.), Boc-alanine (83 mg., 0.44 mmole, 15 min.; 83 mg, 0.44 mmole, 10 min), Boc-O$^\beta$-benzyl-aspartic acid (142 mg, 0.44 mmole, 15 min.; 142 mg, 0.44 mmole, 30 min.), Boc-O-benzylserine (130 mg, 0.44 mmole, 30 min.; 130 mg, 0.44 mmole, 30 min.), and Boc-N$^{im}$-tosylhistidine (180 mg, 0.44 mmole, 15 min.; 190 mg, 0.44 mmole, 30 min.) to give 720 mg of Boc-octacospeptide resin.

This peptide resin was cleaved with the procedure described in Example 2 except that 6 ml dimethylsulfide and 2 ml HF were used in the first step and 0.72 ml anisole and 7 ml HF were used in the second step. The HF was removed in vacuo and the residual gel was washed with ether and ethyl acetate. The residue was extracted with 10% acetic acid and lyophilized to give 290 mg of a white solid.

A portion of this crude material (150 mg) was purified by preparative HPLC as in Example 2. The main peak was collected and lyophilized to yield 39.7 mg (19.3%) of a white, amorphous powder. This compound was homogeneous by HPLC and TLC and gave the correct amino acid analysis.

EXAMPLE 9

Preparation, Purification and Characterization of (Nle$^{17}$, Thr$^{24}$)VIP

A portion of the Boc-asparagine resin (0.4 g, 0.108 mmole) of Example 8 was coupled with twenty-seven individual cycles of Boc-leucine (108 mg, 0.43 mmole, 30 min.; 108 mg, 0.43 mmole, 10 min.), Boc-isoleucine (100 mg, 0.43 mmole, 15 min.; 100 mg, 0.43 mmole, 10 min.) Boc-O-benzyl-serine (127 mg, 0.43 mmole, 15 min.; 127 mg, 0.43 mmole, 10 min.), Boc-O-benzyl-threonine (133 mg, 0.43 mmole, 30 min.; 133 mg, 0.43 mmole, 70 min.; 267 mg, 0.86 mmole, 70 min.), Boc-leucine (108 mg, 0.43 mmole, 15 min.; 108 mg, 0.43 mmole, 120 min.), Boc-O-2,6-dichlorobenzyltyrosine (190 mg, 0.43 mmole, 15 min.; 190 mg, 0.43 mmole, 120 min.), Boc-N$^\epsilon$-2-chlorobenzyloxycarbonyl-lysine (179 mg, 0.43 mmole, 15 min.; 179 mg, 0.43 mmole, 30 min.), Boc-N$^\epsilon$-2-chlorobenzyloxycarbonyl-lysine (179 mg, 0.43 mmole, 15 min.; 179 mg, 0.43 mmole, 10 min.), Boc-valine (94 mg, 0.43 mmole, 30 min.; 94 mg, 0.43 mmole, 10 min.), Boc-alanine, (82 mg, 0.43 mmole, 15 min.; 82 mg, 0.43 mmole, 10 min.), Boc-norleucine (99 mg, 0.43 mmole, 15 min.; 99 mg, 0.43 mmole, 10 min.), Boc-glutamine (58 mg, 0.23 mmole, 30 min.; 58 mg, 0.23 mmole, 30 min.), Boc-N-2-chlorobenzyloxycarbonyl-lysine (179 mg, 0.43 mmole, 15 min.; 179 mg, 0.43 mmole, 10 min.), Boc-N$^G$-tosyl-arginine (185 mg, 0.43 mmole, 15 min.; 185 mg, 0.43 mmole, 60 min.), Boc-leucine (108 mg, 0.43 mmole, 15 min.; 108 mg, 0.43 mmole, 10 min.), Boc-N$^G$-tosyl-arginine (185 mg, 0.43 mmole, 30 min.; 185 mg, 0.43 mmole, 10 min.), Boc-O-benzyl-threonine (133 mg, 0.43 mmole, 15 min.; 133 mg, 0.43 mmole, 10 min.), Boc-O-2,6-dichlorobenzyl-tyrosine (190 mg, 0.43 mg, 15 min.; 190 mg, 0.43 mmole, 10 min.), Boc-asparagine (55 mg, 0.23 mmole, 30 min.; 55 mg. 0.23 mmole, 10 min.), Boc-O$^\beta$-benzyl-aspartic acid (139 mg, 0.43 mmole, 15 min.; 139 mg, 0.43 mmole, 10 min.), Boc-O-benzyl-threonine (133 mg, 0.43 mmole, 15 min.; 133 mg, 0.43 mmole, 10 min.), Boc-phenylalanine (114 mg, 0.43 mmole, 15 min.; 114 mg, 0.43 mmole, 10 min.), Boc-valine (94 mg, 0.43 mmole, 15 min.; 74 mg, 0.43 mmole, 10 min.) Boc-alanine (82 mg, 0.43 mmole, 15 min, 82 mg, 0.43 mmole, 10 min.), Boc-O-benzyl-aspartic acid (139 mg, 0.43 mmole, 15 min.; 139 mg, 0.43 mmole, 10 min.), Boc-O-benzyl-serine (127 mg, 0.43 mmole, 15 min.; 127 mg, 0.43 mmole, 10 min.), and Boc-N-$^{im}$tosylhistidine (174 mg, 0.43 mmole, 30 min.; 174 mg, 0.43 mmole, 10 min.) to give 760 mg of Boc-octacosapeptide resin.

This peptide resin was cleaved with the procedure described in Example 8. The HF was removed in vacuo and the residual solid was washed with ether and ethyl acetate. The residue was extracted with 10% acetic acid and lyophilized to give 320 mg of a white solid.

This crude material was purified by preparative HPLC as in Example 2. The main peak was collected and lyophilized to yield 42 mg (11%) of a white, amorphous powder. This compound was homogeneous by HPLC and TLC and gave the correct amino acid analysis.

EXAMPLE 10

Preparation, Purification and Characterization of (Ala$^9$, Nle$^{17}$)VIP

Benzhydrylamine copolystyrene-2% divinylbenzene cross-linked resin (7.0 g, 4.58 mmole N) was derivatized as in Example 1 with Boc-asparagine (620 mg, 2.67 mmole), 1-hydroxybenzotriazole (492 mg, 3.64 mmole), and dicyclohexylcarbodiimide (499 mg, 2.42 mmole). After washing, the resin was dried under high vacuum to give 8.1 g. Amino acid analysis showed the resin to contain 0.21 mmoles of asparagine/g. Unreacted amine groups were capped with 8.0 ml acetic anhydride and 8.0 ml diisopropylethylamine in methylene chloride for 1 hour and washed as in Example 1.

A portion of this Boc-asparagine resin (7.0 g, 1.47 mmole) was coupled with three individual cycles of Boc-leucine (1.88 g, 7.56 mmole, 30 min.; 1.88 g, 7.56 mmole, 20 min.), Boc-isoleucine (1.75 g, 7.56 mmole, 30 min.; 1.75 g, 7.56 mmole, 20 min.), and Boc-O-benzyl-serine (2.23 g, 7.56 mmole, 20 min.; 2.23 g, 7.56 mmole, 20 min.) to give 8.245 g of Boc-tetrapeptide resin.

A portion of this resin (7.76 g, 1.38 mmole) was coupled with two individual cycles of Boc-asparagine (0.91 g, 3.91 mmole, 40 min.; 0.91 g, 3.91 mmole, 60 min.), and Boc-leucine (1.77 g, 7.12 mmole, 60 min.; 1.77 g, 7.12 mmole, 60 min.) to give 7.57 g of Boc-hexapeptide resin.

A portion of this resin (6.15 g, 1.23 mmole) was coupled with three individual cycles of Boc-O-2,6- dichlorobenzyltyrosine (2.55 g, 5.8 mmole, 30 min.; 2.55 g, 5.8 mmole, 45 min.) Boc-N$^\epsilon$-2-chlorobenzyloxycarbonyl-lysine (2.40 g, 5.8 mmole, 45 min.; 2.40 g, 5.8 mmole, 20 min.), and Boc-N$^\epsilon$-2-chlorobenzyloxycarbonyl-lysine (2.40 g, 5.8 mmole, 30 min.; 2.40 g, 5.8 mmole, 20 min.) to give 2.06 g of Boc-nonapeptide resin.

A portion of this resin (7.44 g, 1.03 mmole) was coupled with five individual cycles of Boc-valine (1.16 g, 5.33 mmole, 30 min.; 1.16 g, 5.33 mmole, 5 min.), Boc-alanine (1.01 g, 5.33 mmole, 30 min.; 1.01 g, 5.33 mmole, 5 min.), Boc-norleucine (1.23 g, 5.33 mmole, 30 min.; 1.23 g, 5.33 mmole, 15 min.), Boc-glutamine (0.72 g, 2.93 mmole, 30 min.; 0.72 g, 2.93 mmole, 30 min.), and Boc-N$^\epsilon$-2-chlorobenzyloxycarbonyl-lysine (2.21 g, 5.33 mmole, 30 min.; 2.21 g, 5.33 mmole, 30 min.) to give 7.80 g of Boc-tetradecapeptide resin.

A portion of this resin (7.15 g, 0.95 mmole) was coupled with one cycle of Boc-N$^G$-tosyl-arginine (2.09 g, 4.88 mmole, 30 min.; 2.09 g, 4.88 mmole, 130 min.) to give 7.93 g of Boc-pentadecapeptide resin.

A portion of this resin (7.21 g, 0.86 mmole) was coupled with one cycle of Boc-leucine (1.10 g, 4.44 mmole, 30 min.; 1.10 g, 4.44 mmole, 30 min.) to give 7.2 g of Boc-hexadecapeptide resin.

A portion of this resin (0.7 g, 0.086 mmole) was coupled with twelve individual cycles of Boc-N$^G$-tosyl-arginine (188 mg, 0.44 mmole, 10 min.; 188 mg, 0.44 mmole, 10 min.), Boc-O-benzyl-threonine (136 mg, 0.44 mmole, 10 min.; 136 mg, 0.44 mmole, 30 min.), Boc-O-2,6-dichlorobenzyl-tyrosine (194 mg, 0.44 mmole, 10 min.; 194 mg, 0.44 mmole, 10 min.), Boc-O$^\beta$-benzyl-aspartic acid (142 mg, 0.44 mmole, 10 min.; 142 mg, 0.44 mmole, 10 min.), Boc-O-benzyl-threonine (136 mg, 0.44 mmole, 10 min; 136 mg, 0.44 mmole, 60 min.), Boc-phenylalanine (116 mg, 0.44 mmole, 10 min.; 116 mg, 0.44 mmole, 10 min.), Boc-valine (95 mg, 0.44 mmole, 10 min.; 95 mg, 0.44 mmole, 10 min.), Boc-alanine (83 mg, 0.44 mmole, 10 min.; 83 mg, 0.44 mmole, 10 min.), Boc-O-benzyl-aspartic acid (142 mg, 0.44 mmole, 10 min.; 142 mg, 0.44 mmole, 10 min.), Boc-O-benzyl-serine (130 mg, 0.44 mmole, 10 min.; 130 mg, 0.44 mmole, 10 min.), and Boc-N$^{im}$-tosyl-histidine (100 mg, 0.44 mmole, 10 min.; 180 mg, 0.44 mmole, 10 min.) to give 0.778 g of Boc-octacosapeptide resin.

EXAMPLE 11

Preparation, Purification and Characterization of (Lys$^{14}$, Nle$^{17}$)VIP

A portion of the Boc-tetradecapeptide resin (0.66 g, 0.078 mmole) of Example 10 was coupled with fourteen individual cycles of Boc-N-2-chlorobenzyloxycarbonyl-lysine (182 mg, 0.44 mmole, 15 min.; 182 mg, 0.44 mmole, 30 min.), Boc-leucine (109 mg, 0.44 mmole, 15 min.; 109 mg, 0.44 mmole, 10 min.), Boc-N$^G$-tosyl-arginine (188 mg, 0.44 mole, 15 min.; 188 mg, 0.44 mmole, 10 min.), Boc-O-benzylthreonine (136 mg, 0.44 mmole, 15 min.; 136 mg, 0.44 mmole, 10 min.), Boc-O-2,6-dichlorobenzyltyrosine (194 mg, 0.44 mmole, 15 min.; 194 mg, 0.44 mmole, 10 min.), Boc-asparagine (56 mg, 0.24 mmole, 15 min.; 56 mg, 0.24 mmole, 45 min.), Boc-O$^\beta$-benzyl-aspartic acid (142 mg, 0.44 mmole, 15 min.; 142 mg, 0.44 mmole, 10 min.). Boc-O-benzyl-threonine (136 mg, 0.44 mmole, 15 min.; 136 mg, 0.44 mmole, 30 min.), Boc-phenylalanine (116 mg, 0.44 mmole, 15 min; 116 mg, 0.44 mmole, 10 min.), Boc-valine (95 mg, 0.44 mmole, 15 min.; 95 mg, 0.44 mmole, 10 min.), Boc-alanine (83 mg, 0.44 mmole, 15 min.; 83 mg, 0.44 mmole, 10 min.), Boc-O$^\beta$-benzyl-aspartic acid (142 mg, 0.44 mmole, 15 min.; 142 mg, 0.44 mmole, 10 min.), Boc-O-benzyl-serine (130 mg, 0.44 mmole, 15 min.; 130 mg, 0.44 mmole, 30 min.), and Boc-N$^{im}$-tosyl-histidine (180 mg, 0.44 mmole, 10 min.; 180 mg, 0.44 mmole, 20 min.) to give 0.78 g of Boc-octacosapeptide resin.

A portion of this peptide resin (397 mg, 0.039 mmole) was cleaved by the procedure described in Example 2. The HF was removed in vacuo and the residue was washed with ether and ethyl acetate. The residue was extracted with 10% acetic acid and lyophilized to give 200 mg of a white solid.

This crude material was purified by preparative HPLC as in Example 2. The main peak was collected and lyophilized to yield 24 mg (17%) of a white, amorphous powder. This compound was homogeneous by HPLC and TLC and gave the correct amino acid analysis.

EXAMPLE 12

Preparation, Purification and Characterization of (Nle$^{17}$, Val$^{26}$, Thr$^{28}$)VIP Boc-O-benzyl-threonine (1.39 g, 4.5 mmole) was dissolved in methylene chloride and chilled to 0° C. While stirring, 464 mg (2.25 mmole) of dicyclohexylcarbodiimide was added. After 30 minutes at 0° C. the precipitate was filtered off. The filtrate was added to 3.0 g (1.5 mmole) of benzhydrylamine copolystyrene-2% divinylbenzene cross-linked resin which was pre-washed as in Example 1. The mixture was stirred at room temperature for 4 hours and washed as in Example 1. The resin was dried under high vacuum to give 3.47 g. Amino acid analysis showed the resin to contain 0.368 mmoles of threonine/g. Unreacted amine groups were capped as in Example 1 with 3.5 ml acetic anhydride and 3.5 ml diisopropylethylamine.

A portion of this Boc-threonine-resin (1.7 g, 0.625 mmole) was coupled with one cycle of Boc-leucine (623 mg, 2.5 mmole, 30 min; 623 mg, 2.5 mmole, 10 min) to give 1.73 g of Boc-dipeptide resin.

A portion of this resin (865 mg, 0.312 mmole) was coupled with twelve individual cycles of Boc-valine (271 mg, 1.25 mmole, 30 min; 271 mg, 1.25 mmole, 10 min.), Boc-O-benzyl-serine (369 mg, 1.25 mmole, 30 min; 369 mg, 1.25 mmole, 10 min), Boc-asparagine (159 mg, 0.687 mmole, 30 min; 159 mg, 0.687 mmole, 30 min.), Boc-leucine (311 mg, 1.25 mmole, 30 min; 311 mg, 1.25 mmole, 60 min), Boc-O-2,6-dichlorobenzyl-tyrosine (550 mg, 1.25 mmole, 30 min; 550 mg, 1.25 mmole, 60 min; 550 mg, 1.25 mmole, 80 min), Boc-N$^\epsilon$-2-chlorobenzyloxycarbonyl-lysine (518 mg, 1.25 mmole, 15 min; 518 mg, 1.25 mmole, 60 min), Boc-N$^\epsilon$-2-chlorobenzyloxycarbonyl-lysine (518 mg, 1.25 mmole, 30 min; 518 mg, 1.25 mmole, 60 min.), Boc-valine (271 mg, 1.25 mmole, 30 min; 271 mg, 1.25 mmole, 10 min), Boc-alanine (236 mg, 1.25 mmole, 15 min; 236 mg, 1.25 mmole, 10 min), Boc-norleucine (289 mg, 1.25 mmole, 15 min; 289 mg, 1.25 mmole, 10 min.), Boc-glutamine (338.5 mg, 1.375 mmole, 120 min) and Boc-N$^\epsilon$-2-chlorobenzyloxycarbonyl-lysine (518 mg, 1.25 mmole, 15 min; 518 mg, 1.25 mmole, 60 min.) to give 1.52 g of Boc-tetradecapeptide resin.

A portion of this peptide resin (760 mg, 0.156 mmole) was coupled with fourteen individual cycles of Boc-N$^G$-tosylarginine (268 mg, 0.63 mmole, 15 min; 268 mg, 0.63 mmole, 120 min; 536 mg, 1.25 mmole, 120 min.), Boc-leucine (156 mg, 0.63 mmole, 15 min; 156 mg, 0.63 mmole, 10 min.), Boc-N$^G$-tosyl-arginine (268 mg, 0.63 mmole, 30 min; 268 mg, 0.63 mmole, 120 min; 536 mg, 1.25 mmole, 360 min), Boc-O-benzyl-threonine (193 mg, 0.63 mmole, 15 min; 193 mg, 0.63 mmole, 60 min; 387 mg, 1.25 mmole, 60 min), Boc-O-2,6-dichlorobenzyl-tyrosine (278 mg, 0.63 mmole, 15 min; 275 mg, 0.63 mmole, 120 min), Boc-asparagine (80 mg, 0.344 mmole, 30 min; 80 mg, 0.344 mmole, 60 min.), Boc-O$^\beta$-benzyl-aspartic acid (202 mg, 0.63 mmole, 15 min; 202 mg, 0.63 mmole, 10 min.), Boc-O-benzyl-threonine (387 mg, 1.25 mmole, 70 min), Boc-phenylalanine (165 mg, 0.63 mmole, 15 min; 165 mg, 0.63 mmole, 10 min), Boc-valine (135 mg, 0.63 mmole, 15 min; 135 mg, 0.63 mmole, 10 min.), Boc-alanine (118 mg, 0.63 mmole, 15 min; 118 mg, 0.63 mmole, 10 min), Boc-O$^\beta$-benzyl-aspartic acid (202 mg, 0.63 mmole, 15 min; 202 mg, 0.63 mmole, 10 min), Boc-O-benzyl-serine (184 mg, 0.63 mmole, 15 min; 156 mg, 0.63 mmole, 10 min.) to give 1.24 g of Boc-octacosapeptide resin.

A portion of this resin (620 mg, 0.078 mmole) was cleaved with the procedure described in Example 2 except that 0.7 ml anisole and 6.3 ml HF were used in the second step. The HF was removed in vacuo and the residual gum was washed with ether and ethyl acetate. The residue was extracted with 10% acetic acid and lyophilized to give 380 mg of a white solid.

A portion of this crude material (119 mg) was purified by preparative HPLC as in Example 2. The main peak was collected and lyophilized to yield 29.3 mg (33.5%) of a white, amorphous powder. This compound was homogeneous by HPLC and TLC and gave the correct amino acid analysis.

EXAMPLE 13

Preparation, Purification and Characterization of (Lys$^{12}$, Lys$^{14}$, Nle$^{17}$, Val$^{26}$, Thr$^{28}$)VIP A portion of the Boc-tetradecapeptide resin (370 mg, 0.076 mmole) of Example 12 was coupled with fourteen individual cycles of Boc-N$^\epsilon$-2-chlorobenzyloxycarbonyl-lysine (127 mg, 0.30 mmole, 15 min; 127 mg, 0.30 mmole, 60 min), Boc-leucine (76 mg, 0.30 mmole, 20 min; 76 mg, 0.30 mmole, 5 min) Boc-N$^\epsilon$-2-chlorobenzyloxycarbonyl-lysine (127 mg, 0.30 mmole, 20 min, 127 mg, 0.30 mmole, 5 min.), Boc-O-benzylthreonine (95 mg, 0.30 mmole, 20 min; 95 mg, 0.30 mmole, 60 min), Boc-O-2,6-dichlorobenzyl-tyrosine (135 mg, 0.30 mmole, 20 min; 135 mg, 0.30 mmole, 60 min), Boc-asparagine (39 mg, 0.16 mmole, 30 min; 39 mg, 0.16 mmole, 60 min), Boc-O$^\beta$-benzyl-aspartic acid (99 mg, 0.30 mmole, 30 min), Boc-O-benzyl-threonine (95 mg, 0.30 mmole, 30 min; 95 mg, 0.30 mmole, 5 min), Boc-phenylalanine (80 mg, 0.30 mmole, 30 min.), Boc-valine (66 mg, 0.30 mmole, 20 min), Boc-alanine (57 mg, 0.30 mmole, 20 min; 57 mg, 0.30 mmole, 10 min), Boc-O$^\beta$-benzyl-aspartic acid (99 mg, 0.30 mmole, 20 min; 99 mg, 0.30 mmole, 60 min), Boc-O-benzyl-serine (90 mg, 0.30 mmole, 20 min; 90 mg, 0.30 mmole, 5 min.), and Boc-N$^{im}$-tosylhistidine (124 mg, 0.30 mmole, 20 min; 124 mg, 0.30 mmole, 10 min) to give 0.65 g of Boc-octacosapeptide resin.

A portion of this resin (0.3 g, 0.35 mmole) was cleaved with the procedure described in Example 2. The HF was removed in vacuo and the residue was washed with ether and ethyl acetate. The residue was extracted with 10% acetic acid and lyophilized to give 140 mg of a yellow solid.

This crude material was purified by preparative HPLC as in Example 2. The main peak was collected and lyophilized to yield 13.0 mg (10.5%) of a white, amorphous powder. This compound was homogeneous by HPLC and TLC and gave the correct amino acid analysis.

EXAMPLE 14

Preparation, Purification and Characterization of (Nle$^{17}$, Thr$^{28}$)VIP

A portion of the Boc-dipeptide resin (0.865 g, 0.312 mmole) of Example 12 was coupled with twelve individual cycles of Boc-isoleucine (289 mg, 1.25 mmole, 30 min; 289 mg, 1.25 mmole, 10 min.), Boc-O-benzyl-serine (369 mg, 1.25 mmole, 30 min; 369 mg, 1.25 mmole, 10 min.), Boc-asparagine (159 mg, 0.687 mmole, 45 min; 159 mg, 0.687 mmole, 30 min), Boc-leucine (311 mg, 1.25 mmole, 45 min; 311 mg, 1.25 mmole, 60 min), Boc-O-2,6-dichlorobenzyl-tyrosine (550 mg, 1.25 mmole, 60 min; 550 mg, 1.25 mmole, 90 min), Boc-N$^\epsilon$-2-chlorobenzyloxycarbonyl-lysine (518 mg, 1.25 mmole, 30 min; 518 mg, 1.25 mmole, 90 min), Boc-N$^\epsilon$-2-chlorobenzyloxycarbonyl-lysine (518 mg, 1.25 mmole, 30 min; 518 mg, 1.25 mmole, 60 min), Boc-valine (271 mg, 1.25 mmole, 30 min; 271 mg, 1.25 mmole, 60 min), Boc-alanine (236 mg, 1.25 mmole, 30 min; 236 mg, 1.25 mmole, 10 min), Boc-norleucine (289 mg, 1.25 mmole, 30 min; 289 mg, 1.25 mmole, 10 min), Boc-glutamine (169 mg, 0.687 mmole, 30 min; 169 mg, 0.687 mmole, 10 min), and Boc-N$^\epsilon$-2-chlorobenzyloxycarbonyl-lysine (518 mg, 1.25 mmole, 30 min; 518 mg, 1.25 mmole, 10 min) to give 1.2 g of Boc-tetradecapeptide resin.

A portion of this resin (0.6 g, 0.156 mmole) was coupled with fourteen individual cycles of Boc-N$^G$-tosyl-arginine (268 mg, 0.63 mmole; 30 min; 268 mg, 0.63 mmole, 360 min; 536 mg, 1.25 mmole, 120 min), Boc-leucine (156 mg, 0.63 mmole, 15 min; 156 mg, 0.63 mmole, 60 min), Boc-N$^G$-tosyl-arginine (268 mg, 0.63 mmole, 30 min; 268 mg, 0.63 mmole, 60 min; 268 mg, 0.63 mmole, 90 min), Boc-O-benzyl-threonine (387 mg, 1.25 mmole, 120 min), Boc-O-2,6-dichlorobenzyl-tyrosine (275 mg, 0.63 mmole, 30 min; 275 mg, 0.63 mmole, 10 min.), Boc-asparagine (80 mg, 0.34 mmole, 30 min; 30 mg, 0.34 mmole, 60 min), Boc-O$^\beta$-benzyl-aspartic acid (404 mg, 1.25 mmole, 60 min.), Boc-O-benzyl-threonine (193 mg, 0.63 mmole; 15 min.; 193 mg, 0.63 mmole, 60 min), Boc-phenylalanine (165 mg, 0.63 mmole, 15 min; 165 mg, 0.63 mmole, 30 min), Boc-valine (271 mg, 1.25 mmole, 60 min), Boc-alanine (118 mg, 0.63 mmole, 15 min; 118 mg, 0.63 mmole, 10 min.), Boc-O-$\beta$-benzyl-aspartic acid (202 mg, 0.63 mmole, 15 min; 202 mg, 0.63 mmole, 10 min), Boc-O-benzyl-serine (184 mg, 0.63 mmole, 15 min; 184 mg, 0.63 mmole, 10 min), and Boc-N$^{im}$-tosyl-histidine (256 mg, 0.63 mmole, 15 min; 256 mg, 0.63 mmole, 10 min) to give 1.1 g of Boc-octacosapeptide resin.

A portion of this resin (0.55 g, 0.078 mmole) was cleaved with the procedure described in Example 2 except that 0.6 ml anisole and 5.4 ml HF were used in the second step. The HF was removed in vacuo and the residue was washed with ether and ethyl acetate. The residue was extracted with 10% acetic acid and lyophilized to give 275 mg of a white solid.

A portion of this crude material (80 mg) was purified by preparative HPLC as in Example 2. The main peak was collected and lyophilized to yield 15 mg (18.4%) of a white, amorphous powder. This compound was homogeneous by HPLC and TLC and gave the correct amino acid analysis.

EXAMPLE 15

Preparation, Purification and Characterization of (Lys$^{12}$, Nle$^{17}$, Val$^{26}$, Thr$^{28}$)VIP A portion of the Boc-threonine resin (0.7 g, 0.25 mmole) of Example 12 was coupled with thirteen individual cycles of Boc-leucine (257 mg, 1.03 mmole, 45 min; 257 mg, 1.03 mmole, 10 min.), Boc-valine (223 mg, 1.03 mmole, 20 min; 223 mg, 1.03 mmole, 20 min), Boc-O-benzyl-serine (304 mg, 1.03 mmole, 45 min; 304 mg, 1.03 mmole, 10 min), Boc-asparagine (131 mg, 0.56 mmole, 105 min; 131 mg, 0.56 mmole, 30 min), Boc-leucine (257 mg, 1.03 mmole, 15 min; 257 mg, 1.03 mmole, 60 min), Boc-O-2,6-dichlorobenzyltyrosine (453 mg, 1.03 mmole, 45 min; 453 mg, 1.03 mmole, 120 min), Boc-N$^\epsilon$-2-chlorobenzyloxy-carbonyl-lysine (427 mg, 1.03 mmole, 45 min; 427 mg, 1.03 mmole, 10 min), Boc-N$^\epsilon$-2-chlorobenzyloxycarbonyl-lysine (427 mg, 1.03 mmole, 30 min; 427 mg, 1.03 mmole, 20 min), Boc-valine (223 mg, 1.03 mmole, 30 min; 223 mg, 1.03 mmole, 20 min), Boc-alanine (195 mg, 1.03 mmole, 30 min; 195 mg, 1.03 mmole, 10 min), Boc-norleucine (238 mg, 1.03 mmole, 15 min; 238 mg, 1.03 mmole, 10 min), Boc-glutamine (278 mg, 1.13 mmole, 120 min), and Boc-N$^\epsilon$-2-chlorobenzyloxycarbonyl-lysine (427 mg, 1.03 mmole, 70 min; 427 mg, 1.03 mmole, 10 min) to give 1.4 g of Boc-tetradecapeptide resin.

A portion of this resin (0.7 g, 0.12 mmole) was coupled with fourteen individual cycles of Boc-N$^G$-tosyl-arginine (220 mg, 0.52 mmole, 30 min; 220 mg, 0.52 mmole, 120 min), Boc-leucine (128 mg, 0.52 mmole, 20 min; 128 mg, 0.52 mmole, 10 min), Boc-N$^\epsilon$-2-chlorobenzyloxycarbonyl-lysine (214 mg, 0.52 mmole, 15 min; 214 mg, 0.52 mmole, 30 min), Boc-O-benzylthreonine (159 mg, 0.52 mmole, 15 min; 159 mg, 0.52 mmole, 120 min), Boc-O-2,6-dichlorobenzyl-tyrosine (227 mg, 0.52 mmole, 15 min; 227 mg, 0.52 mmole, 30 min), Boc-asparagine (66 mg, 0.28 mmole, 30 min; 66 mg, 0.28 mmole, 20 min), Boc-O$^\beta$-benzyl-aspartic acid (166 mg, 0.52 mmole, 15 min; 166 mg, 0.52 mmole, 20 min), Boc-O-benzyl-threonine (159 mg, 0.52 mmole, 15 min; 159 mg, 0.52 mmole, 30 min), Boc-phenylalanine (136 mg, 0.52 mmole, 15 min; 136 mg, 0.52 mmole, 10 min), Boc-valine (224 mg, 1.03 mmole, 30 min), Boc-alanine (97 mg, 0.52 mmole, 15 min; 97 mg, 0.52 mmole, 10 min), Boc-O$^\beta$-benzyl-aspartic acid (166 mg, 0.52 mmole, 15 min; 166 mg, 0.52 mmole, 10 min), Boc-O-benzyl-serine (152 mg, 0.52 mmole, 15 min; 152 mg, 0.52 mmole, 10 min.), and Boc-N$^{im}$-tosyl-histidine (208 mg, 0.52 mmole, 15 min; 208 mg, 0.52 mmole, 10 min.) to give 0.72 g of Boc-octacosapeptide resin.

A portion of this resin (0.4 g, 0.066 mmole) was cleaved with the procedure described in Example 2 except that 0.4 ml anisole and 3.6 ml HF were used in the second step. The HF was removed in vacuo and the residue was washed with ether and ethyl acetate. The residue was extracted with 10% acetic acid and lyophilized to give 227 mg of a white solid.

This crude material was purified by preparative HPLC as in Example 2. The main peak was collected and lyophilized to yield 32 mg (13.5%) of a white, amorphous powder. This compound was homogeneous by HPLC and TLC and gave the correct amino acid analysis.

EXAMPLE 16

Bronchodilator Activity of VIP Analogs

The bronchodilatory effect of VIP analogs was studied in a model utilizing guinea pig trachea. Wasserman, M. A. et al. "Comparative In Vitro Tracheal Relaxant Effects of Porcine and Hen VIP" in *Vasoactive Intestinal Peptide* ed. Said, S.I., Raven Press (New York, 1982).

All tissues were taken from male albino guinea pigs weighing 400–600 g, anesthetized with urethane 2 g/kg i.p. After exsanguination the trachea was removed and divided into four ring segments (3 mm length). Each ring was suspended by two 30 guage stainless steel wires in a 10 ml jacket tissue bath and attached via 4-0 silk thread to a Grass force displacement transducer (model FT03C, Grass Instrument Co., Quincy, MA), for isometric recording of tension. The smooth muscle was bathed in modified Krebs solution of the following composition: NaCl, 120 mM; KCl, 4.7 mM; $CaCl_2$, 2.5 mM; $MgSO_4.7H_2O$; 1.2 mM; $NaHCO_3$, 25 mM; $KH_2PO_4$ monobasic, 1.2 mM; and dextrose, 10 mM. Tissue baths were maintained at 37.5° C. and constantly bubbled with 95% $O_2$ and 5% $CO_2$. Responses were recorded on an 8 channel and 4 channel Hewlett-Packard (model 7702B and 7754A, respectively) recorder (Hewlett Packard, Paramus, NJ). Tracheal rings were placed under a resting tension of 1.5 g which was determined to be at or near optimal in preliminary experiments. Frequent readjustments of tension were required during the 60 min. stabilization period which followed. Tissues were rinsed at 15 min. intervals.

Cumulative concentration response curves were obtained for each tissue by successive $\mu l$ increases in the bath concentration of VIP or potential VIP agonists according to the method of VanRossum J. M., *Arch. Int Pharmacodyn*, 143, 299–330 (1963). Only one cummulative dose response curve was obtained on a single piece of tissue. To minimize variability between tissues, relaxant responses are expressed as a percentage of the maximum response obtainable to VIP ($10^{-6}M=100\%$) added at the end of the concentration response curve. Responses obtained from three tissues were pooled and $EC_{50}$ values were determined by linear regression.

The results summarized in Table I show that the VIP analogs possess potent bronchodilator activity. The potencies of these analogs have been found to be equal to or greater than native VIP.

TABLE I

Bronchodilator effect of VIP analogs on guinea pig trachea smooth muscle
AGONIST ACTIVITY

| Compound | $EC_{50}$ (M) | Relative Potency |
|---|---|---|
| VIP | $1.0 \times 10^{-8}$ | 100% |
| Ac—(Nle$^{17}$)—VIP | $9.0 \times 10^{-9}$ | 111 |
| (Nle$^{17}$)—VIP | $6.4 \times 10^{-9}$ | 156 |
| (Orn$^{12}$, Nle$^{17}$)—VIP | $5.0 \times 10^{-9}$ | 200 |
| (Lys$^{12}$, Nle$^{17}$)—VIP | $3.8 \times 10^{-9}$ | 263 |
| Ac—(Ser$^{11}$, Phe$^{13}$, Nle$^{17}$)—VIP | $2.2 \times 10^{-8}$ | 45 |
| Ac—(Lys$^{12}$, Nle$^{17}$)—VIP | $1.5 \times 10^{-8}$ | 67 |
| (Ala$^9$, Nle$^{17}$)—VIP | $1.0 \times 10^{-8}$ | 100 |
| (Nle$^{17}$, Thr$^{25}$)—VIP | $9.9 \times 10^{-9}$ | 101 |
| (Nle$^{17}$, Thr$^{28}$)—VIP | $9.3 \times 10^{-9}$ | 108 |
| (Nle$^{17}$, Thr$^{24}$)—VIP | $8.0 \times 10^{-9}$ | 125 |
| (Lys$^{12}$, Lys$^{14}$, Nle$^{17}$, Val$^{26}$, Thn$^{28}$)—VIP | $7.0 \times 10^{-9}$ | 143 |
| (Lys$^{14}$, Nle$^{17}$)—VIP | $5.8 \times 10^{-9}$ | 172 |
| (Nle$^{17}$, Val$^{26}$, Thr$^{28}$)—VIP | $4.8 \times 10^{-9}$ | 208 |
| (Lys$^{12}$, Nle$^{17}$, Val$^{26}$, Thr$^{28}$)—VIP | $3.5 \times 10^{-9}$ | 286 |

EXAMPLE 17

Inhibition of Histamine Induced Bronchoconstriction by Aerochamber

Male guinea pigs (Hartley Strain) weighing 400 to 600 g are anesthetized with urethane (2 μg/kg) intraperitoneally and a polyethylene cannula is inserted into the jugular vein for drug administration. A cannula is inserted in the trachea and connected to an aerochamber for aerosol administration of test drug. Spontaneously breathing animals are exposed for a 30 second period to varying concentrations of aerosol solution of test drug or appropriate placebo sprayed into the aerochamber (2-10 inhalations). Metered dose inhalers are used to administer all compounds by inhalation. Each 5 ml inhaler contains 50 metered doses (100 μl per actuation) each delivering 0.04 mg of test drug. An excipient formulation consists of 0.01 ml dimethylsulfoxide, 0.5 ml ethanol and 4.49 ml freon 12. At the end of the 30 second exposure period, the animals are paralyzed with succinylcholine (1.2 mg/kg, i.v.) and mechanically respirated (Harvard rodent respirator) at 40 breaths/min and 3 cc tidal volume. Tracheal pressure is recorded on a two channel polygraph (Hewlett-Packard Model 77028) from a cannula inserted in the trachea and connected to a Statham presure transducer (P23 DB). Animals are challenged with a maximal constrictory dose of histamine (50 μg/kg, i.v.) delivered 30 seconds after administration of the succinylcholine. The change in ventilatory pressure is determined for controls and drug treated animals. From these numbers, the percent inhibition (mean±SEM) is calculated and $IC_{50}$ determined.

In order to determine the aerosol time course of activity of a drug, the animals are prepared as described above, except that the time between exposure and challenge with histamine varies from 30 seconds to either 5, 10, 20, 30 or 60 minutes.

EXAMPLE 18

Relaxation of Human Bronchial Smooth Muscle

Human bronchial smooth muscle or intra-pulmonary arteries were obtained from surgical section or autopsy from Overlook Hospital, Summit, N.J. Airway or vascular rings were suspended by two 30 gauge stainless steel wires in a 10 ml jacket tissue bath and attached via 4-0 silk thread to a Grass forcer displacement transducer (model FT030C, Grass Instrument Co., Quincy, MA), for isometric recording of tension. The smooth muscle was bathed in modified Kreb's solution of the following composition: NaCl, 120 mM; KCl, 4.7 mM; $CaCL_2$, 2.5 mM; $MgSO_4.7H_2O$; 1.2 mM; $NaHCO_3$, 25 mM; $KH_2PO_4$ monobasic, 1.2 mM; and dextrose, 10 mM. Tissue baths were maintained at 37.5° C. and constantly bubbled with 95% $O_2$ and 5% $CO_2$. Responses were recorded on a 8 channel and 4 channel Hewlett-Packard (model 7702B and 7754A, respectively) recorder (Hewlett Packard, Paramus, NJ). All tissues were placed under a resting tension (airway, 1.5 g; vascular, 1 g) which was determined to be near optimal in preliminary experiments. Frequent readjustments of tension were required during the 120-180 min. stabilization period which followed. Tissues were rinsed at 15 min. intervals. Vascular tissues were primed once with phenylephrine ($10^{-5}$M) and washed for an additional hour. Steady state contractions of vacular tissues were obtained with phenylephrine ($10^{-5}$M) while airway tissues were precontracted with histamine ($3 \times 10^{-4}$M).

Cumulative concentration response curves were obtained for each tissue by successive μl increases in the bath concentration of VIP or potential VIP agonists according to the method of VanRossum noted above. Only one cumulative dose response curve was obtained on a single piece of tissue. To minimize variability between tissues, relaxant responses were expressed as a percentage of the maximum response obtainable to papaverine (vascular, $10^{-4}$M=100%) or isoproterenol (airway, $10^{-4}$M=100%) added at the end of the concentration response curve. Any tissue which did not relax 15 divisions (¾ g) was omitted. Responses obtained from four tissues were pooled and $EC_{50}$ values were determined by linear regression.

The results summarized in Table II show that the VIP analogs possess high bronchodilator activity. The potencies of these analogs have been found to be equal to or greater than native VIP.

TABLE II

Bronchodilator effect of VIP Analogs on Human Bronchial Smooth Muscle
AGONIST ACTIVITY

| Compound | $EC_{50}$ (M) | (n) | Rel. Potency |
| --- | --- | --- | --- |
| VIP (1-28) | 8.400 | (2) | 100% |
| ($Nle^{17}$)—VIP | 3.900 | (3) | 215% |
| ($Orn^{12}$,$Nle^{17}$)—VIP | 4.300 | (3) | 195% |
| Ac—($Nle^{17}$)—VIP | 0.300 | (1) | 2800% |
| ($Lys^{12}$,$Nle^{17}$)—VIP | 5.1 | (2) | 165% |

<sup>a</sup>Steady state contracting of the human bronchi was elicited by $3 \times 10^{-4}$M histamine.

Results from the human in vitro experiments have shown that while VIP is a weak relaxant of tracheal tissue several of the VIP analogs are highly potent.

We claim:

1. A compound of the formula

X-His-Ser-Asp-Ala-Val-Phe-Thr-Asp-R-Tyr-$R_1$-Lys-Gln-$R_2$-Ala-Val-Lys-Lys-Tyr-Leu-$R_3$-Leu-$R_4$ wherein R represents Asn or Ala; $R_1$ represents Thr-Arg-Leu-Arg, Thr-Lys-Leu-Lys, Thr-Arg-Leu-Lys, Thr-Orn-Leu-Arg, Ser-Arg-Phe-Arg or Thr-Lys-Leu-Arg; $R_2$ represents Leu, Ile or Nle; $R_3$ represents Asn-Ser-Ile, Asn-Thr-Ile, Thr-Ser-Ile or Asn-Ser-Val; $R_4$ represents Asn-$NH_2$ or Thr-$NH_2$; and X represents hydrogen or acetylation at the amino terminal, provided that when $R_1$ is Thr-Arg-Leu-Arg, R may not equal Nle, and the pharmaceutically acceptable acid or base addition salts thereof.

2. The compound of claim 1 wherein $R_2$ is norleucine and R, $R_1$, $R_3$, $R_4$ and X are as in claim 1.

3. The compound of claim 1 wherein x represents acetylation and $R_2$ is Nle and R, $R_1$, $R_3$ and $R_4$ are as in claim 1.

4. The compound of claim 2 which is ($Ala^9$, $Nle^{17}$)VIP.

5. The compound of claim 2 which is ($Nle^{17}$, $Thr^{25}$)VIP.

6. The compound of claim 2 which is ($Nle^{17}$, $Thr^{28}$)VIP.

7. The compound of claim 2 which is ($Nle^{17}$, $Thr^{24}$)VIP.

8. The compound of claim 2 which is ($Lys^{14}$, $Nle^{17}$)VIP.

9. The compound of claim 2 which is (Orn$^{12}$, Nle$^{17}$)VIP.

10. The compound of claim 2 which is (Nle$^{17}$, Val$^{26}$, Thr$^{28}$)VIP.

11. The compound of claim 2 which is (Lys$^{12}$, Nle$^{17}$)VIP.

12. The compound of claim 2 which is (Ser$^{11}$, Phe$^{13}$, Nle$^{17}$)-VIP.

13. The compound of claim 2 which is (Lys$^{12}$, Nle$^{17}$, Val$^{26}$, Thr$^{28}$)VIP.

14. The compound of claim 3 which is Ac-(Nle$^{17}$)-VIP.

15. The compound of claim 3 which is Ac-(Lys$^{12}$, Nle$^{17}$)VIP.

16. The compound of claim 3 which is Ac-(Ser$^{11}$, Phe$^{13}$, Nle$^{17}$)VIP.

17. The compound of claim 2 which is (Lys$^{12}$, Lys$^{14}$, Nle$^{17}$, Val$^{26}$, Thr$^{28}$)VIP.

18. A pharmaceutical composition for the treatment of bronchotracheal constriction disorders in humans comprising a compound of the formula

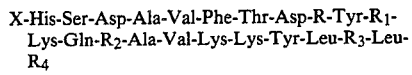
Lys-Gln-R$_2$-Ala-Val-Lys-Lys-Tyr-Leu-R$_3$-Leu-R$_4$ wherein R represents Asn or Ala; R$_1$ represents Thr-Arg-Leu-Arg, Thr-Lys-Leu-Lys, Thr-Arg-Leu-Lys, Thr-Orn-Leu-Arg, Ser-Arg-Phe-Arg or Thr-Lys-Leu-Arg; R$_2$ represents Leu, Ile or Nle; R$_3$ represents Asn-Ser-Ile, Asn-Thr-Ile, Thr-Ser-Ile or Asn-Ser-Val; R$_4$ represents Asn-NH$_2$ or Thr-NH$_2$; and X represents hydrogen or acetylation at the amino terminal, provided that when R$_1$ is Thr-Arg-Leu-Arg, R$_2$ may not equal Nle, in an amount sufficient to relax bronchotracheal smooth muscle and a pharmaceutically acceptable carrier.

19. A pharmaceutical composition for the treatment of bronchotracheal constriction disorders in humans comprising a compound of the formula

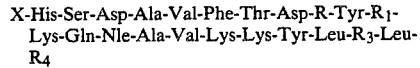
Lys-Gln-Nle-Ala-Val-Lys-Lys-Tyr-Leu-R$_3$-Leu-R$_4$ wherein R represents Asn or Ala; R$_1$ represents Thr-Lys-Leu-Lys, Thr-Arg-Leu-Lys, Thr-Orn-Leu-Arg, Ser-Arg-Phe-Arg or Thr-Lys-Leu-Arg; R$_2$ represents Leu, Ile or Nle; R$_3$ represents Asn-Ser-Ile, Asn-Thr-Ile, Thr-Ser-Ile or Asn-Ser-Val; R$_4$ represents Asn-NH$_2$ or Thr-NH$_2$; and X represents hydrogen or acetylation at the amino terminal, in an amount sufficient to relax bronchotracheal smooth muscle and a pharmaceutically acceptable carrier.

20. A pharmaceutical composition for the treatment of bronchotracheal constriction disorders in humans according to claim 19 wherein in said compound, X represents acetylation at the amino terminal.

21. The pharmaceutical composition of claim 18 wherein the pharmaceutically acceptable carrier is suitable for aerosol administration.

22. The pharmaceutical composition of claim 19 wherein the pharmaceutically acceptable carrier is suitable for aerosol administration.

23. The pharmaceutical composition of claim 20 wherein the pharmaceutically acceptable carrier is suitable for aerosol administration.

24. A method of treating bronchotracheal constriction disorders which comprises administering a compound of the formula

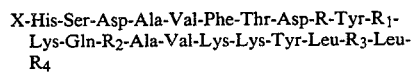
Lys-Gln-R$_2$-Ala-Val-Lys-Lys-Tyr-Leu-R$_3$-Leu-R$_4$ wherein R represents Asn or Ala; R$_1$ represents Thr-Arg-Leu-Arg, Thr-Lys-Leu-Lys, Thr-Arg-Leu-Lys, Thr-Orn-Leu-Arg, Ser-Arg-Phe-Arg or Thr-Lys-Leu-Arg; R$_2$ represents Leu, Ile or Nle; R$_3$ represents Asn-Ser-Ile, Asn-Thr-Ile, Thr-Ser-Ile or Asn-Ser-Val; R$_4$ represents Asn-NH$_2$ or Thr-NH$_2$; and X represents hydrogen or acetylation at the amino terminal, provided that when R$_1$ is Thr-Arg-Leu-Arg, or R$_2$ may not equal Nle in an amount sufficient to relax bronchotracheal smooth muscle.

25. A method of treating bronchotracheal constriction disorders according to claim 25 wherein R$_2$ is Nle.

26. A method of treating bronchotracheal constriction disorders according to claim 25 wherein X represents acetylation at the amino terminal.

27. The method of claim 24, wherein the method of treatment is by aerosol.

28. The method of claim 25, wherein the method of treatment is by aerosol.

29. The method of claim 26, wherein the method of treatment is by aerosol.

* * * * *